Figure 2:
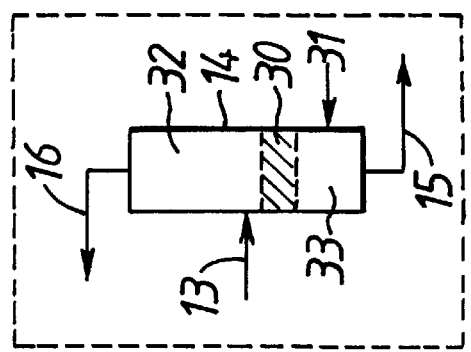

United States Patent [19]
Watson et al.

[11] Patent Number: 5,831,120
[45] Date of Patent: Nov. 3, 1998

[54] PROCESS FOR THE PRODUCTION OF ACETIC ACID

[76] Inventors: Derrick John Watson, Glenfield, Edenfield Estate, Hornsea, East Yorkshire, United Kingdom, HU18 1UE; Bruce Leo Williams, Fairhaven, 36 Stockbridge Road, Ellloughton Brough, East Yorkshire, United Kingdom, HU15 1HN; Michael James Muskett, 23 Denton Street, Beverley, Humberside, United Kingdom, HU17 OPX; Stephen James Smith, 6 Park Lane, Cottingham, North Humberside, United Kingdom, HU16 5RD; Chuc Tu Nguyen, 15915 Windom Dr., Webster, Tex. 77598; Larry Irvin Baker, 122 6th Ave. North, Texas City, Tex. 77590

[21] Appl. No.: 752,330

[22] Filed: Nov. 19, 1996

[51] Int. Cl.$^6$ .............................. C07C 51/12; C07C 53/08
[52] U.S. Cl. ......................... 562/519; 562/607; 562/609; 502/158
[58] Field of Search ................................. 562/519, 607, 562/609; 502/158

[56] References Cited

U.S. PATENT DOCUMENTS

| | | |
|---|---|---|
| 3,769,177 | 10/1973 | Eubanks et al. .......................... 203/71 |
| 3,791,935 | 2/1974 | Eubanks et al. .......................... 203/74 |
| 4,008,131 | 2/1977 | Price ....................................... 203/82 |
| 4,102,922 | 7/1978 | Price ....................................... 260/532 |
| 5,416,237 | 5/1995 | Aubigne et al. ........................ 562/519 |
| 5,599,976 | 2/1997 | Scates et al. ............................ 562/519 |

FOREIGN PATENT DOCUMENTS

| | | |
|---|---|---|
| 105885 | 4/1984 | European Pat. Off. . |
| 473688 | 3/1992 | European Pat. Off. . |
| 616997 | 9/1994 | European Pat. Off. . |
| 643034 | 3/1995 | European Pat. Off. . |
| 728729 | 8/1996 | European Pat. Off. . |
| 1505336 | 3/1978 | United Kingdom . |

OTHER PUBLICATIONS

"$C_1$ to Acetyls: Catalysis and Process"; *Catalysis Today;* M. J. Howard et al.; vol. 18, pp. 325–354; ©1993.

"Katapak: Catalysts and Catalyst Supports with Open Cross-flow Structure"; Sulzer Chemtech; undated.

*Primary Examiner*—Gary Geist
*Assistant Examiner*—Rosalynd Keys
*Attorney, Agent, or Firm*—Fay, Sharpe, Beall, Fagan, Minnich & McKee

[57] ABSTRACT

In the process for the production of acetic acid by carbonylation of methanol and/or a reactive derivative thereof the water concentration in the liquid reaction composition is maintained at a steady-state concentration by at least one process step selected from the group consisting of (i) recovery and disposing of water from at least part of the overhead process stream from the light ends column and (ii) replacing at least a portion of the methanol feed with a component selected from the group consisting of methyl acetate, dimethyl ether, acetic anhydride and mixtures thereof. The recovered aqueous effluent from this and other processes may be purified of carboxylic acid by reactive distillation with at least one $C_1$ to $C_3$ alcohol.

27 Claims, 1 Drawing Sheet

PROCESS FOR THE PRODUCTION OF ACETIC ACID

This invention relates to a process for the production of acetic acid and to a method of purifying carboxylic acid-contaminated aqueous effluents from this and other processes.

Continuous liquid-phase processes for the production of acetic acid by the carbonylation of methanol and/or a reactive derivative thereof in the presence of a Group VIII noble metal catalyst are known. In such processes the acetic acid product is recovered from the liquid reaction composition and dried; the remaining components of the reaction composition being recycled to the reactor to maintain their concentrations therein.

Howard et al in Catalysis Today, 18 (1993) 325–354 describe rhodium and iridium catalysed carbonylation of methanol to acetic acid. The continuous rhodium-catalysed, homogeneous methanol carbonylation process is said to consist of three basic sections; reaction, purification and off-gas treatment. The reaction section comprises a stirred tank reactor, operated at elevated temperature and pressure, and a flash vessel. Liquid reaction composition is withdrawn from the reactor and is passed through a flashing valve to the flash tank where the majority of the lighter components of the liquid reaction composition (methyl iodide, methyl acetate and water) together with product acetic acid are vaporised. The vapour fraction is then passed to the purification section whilst the liquid fraction (comprising the rhodium catalyst in acetic acid) is recycled to the reactor (see FIG. 2 of Howard et al). The purification section is said to comprise a first distillation column (the light ends column), a second distillation column (the drying column) and a third distillation column (the heavy ends column) (see FIG. 3 of Howard et al). In the light ends column methyl iodide and methyl acetate are removed overhead along with some water and acetic acid. The vapour is condensed and allowed to separate into two phases in a decanter, both phases being returned to the reactor. Wet acetic acid is removed from the light ends column as a side draw and is fed to the drying column where water is removed overhead and an essentially dry acetic acid stream is removed from the base of the distillation zone. From FIG. 3 of Howard et al. it can be seen that the overhead water stream from the drying column is recycled to the reaction section. Heavy liquid by-products are removed from the base of the heavy ends column with product acetic acid being taken as a side stream.

It has been found in processes in which methanol and/or a reactive derivative thereof is carbonylated in a liquid reaction composition in a reactor in the presence of a Group VIII noble metal catalyst, a halogen containing co-catalyst and a finite concentration of water, and in which liquid reaction composition is withdrawn from the reactor, carbonylation products are separated therefrom and the remaining components, including water, are recycled to the reactor, that water may accumulate to an unacceptable extent in the recycle streams and thence in the carbonylation reactor.

The accumulation of water can be a problem with iridium-catalysed carbonylation of methanol and/or a reactive derivative thereof to produce acetic acid, because the rate of generation of water by methanation of the methanol and/or reactive derivative in the carbonylation reactor is relatively high and can be greater than the rate of consumption of water by the water gas shift reaction in the carbonylation reactor. The methanation reaction for methanol is shown in formula (I):

$$CH_3OH+H_2 \rightarrow CH_4+H_2O \tag{I}$$

The water gas shift reaction is shown in formula (II):

$$CO+H_2O \rightarrow CO_2+H_2 \tag{II}$$

When rhodium is used as Group VIII noble metal catalyst for the homogeneous carbonylation of methanol and/or a reactive derivative thereof, the methanation reaction is relatively slow and, since water is consumed more quickly by the water gas shift reaction, it is typically necessary to provide a water feed to the system to maintain a steady-state concentration of water in the liquid reaction composition in the reactor.

Water may also accumulate in continuous carbonylation processes by direct and/or indirect ingress of water into the reactor through leaks such as from pump seals and/or condensers or coolers which use water as coolant.

A further problem may arise during start-ups and upsets of continuous liquid phase methanol carbonylation processes when acetic acid having unacceptably high levels of water may be produced. Such off-specification, water-contaminated acetic acid may be purified by feeding a process stream of water-contaminated acetic acid to the process, for example to the drying column of the process, from which water is recycled to the carbonylation reactor. When iridium is used as catalyst this leads to a further accumulation of water in the liquid reaction composition in the carbonylation reactor. When rhodium is used as catalyst the rate at which the water-contaminated, off-specification acetic acid may be fed to the process is limited by the rate at which water is consumed by the water gas shift reaction in the carbonylation reactor, otherwise water will accumulate in the liquid reaction composition in the carbonylation reactor.

The removal of excess water which tends to build up in recycle streams in carbonylation processes for the production of acetic acid is described in U.S. Pat. No. 4,008,131. The acetic acid produced in such a process is said to be purified of water and residual amounts of iodine contaminants by a series of distillations. Water is said to be removable by, for example, the techniques described in U.S. Pat. No. 3,769,177 and U.S. Pat. No. 3,791,935. However, it is said that the water can not be removed by such techniques without the simultaneous removal of the alkyl iodide such as methyl iodide because methyl iodide is said to be taken overhead with the water. It is stated in U.S. Pat. No. 4,008,131 that since the economics dictate that the methyl iodide must be reused, the water-methyl iodide stream is generally recycled to the reactor. It is also said that this stream has to be recycled to recover acid values. According to U.S. Pat. No. 4,008,131 this operation is satisfactory until water build up in the system, due to lack of reaction as well as leaks, resulting in excess amounts of water in the feed to the drying column which create a bottleneck in the drying operation, forcing a cutback in rates which considerably slows down production of pure acid. One obvious corrective action to reduce the water content of the feed is said in U.S. Pat. No. 4,008,131, to be to discard water from the overhead stream. However, discarding water is said also to mean discarding methyl iodide and is said to create a disposal problem in addition to the adverse economic effect resulting when methyl iodide is not recycled. The solution to this problem proposed by U.S. Pat. No. 4,008,131 is to remove a liquid side-stream containing a minor amount of water, some acetic acid and no methyl iodide from a distillation column which is used to purify the acetic acid product; the side-stream, it is said, can be disposed of or rectified at low cost as desired. Thus, U.S. Pat. No. 4,008,131 removes and rejects water as a liquid side-stream from a distillation column in which acetic acid product is recovered.

The removal of water as a side-stream from a distillation column used to purify the acetic acid product is also described in GB 1,505,336.

A disadvantage of the removal of water as a side stream from a distillation column used to purify the acetic acid carbonylation product is that this places constraints on the composition of the process stream which is being withdrawn, which are dependent upon the requirements of the acetic acid purification column.

There is therefore a need for a liquid phase carbonylation process which overcomes the problems of water accumulation in the liquid reaction composition in the carbonylation reactor and enables a steady-state water concentration to be maintained in the liquid reaction composition in the carbonylation reactor without such a disadvantage.

Thus, according to the present invention there is provided a process for the production of acetic acid by the carbonylation of methanol and/or a reactive derivative thereof which process comprises the steps of:

(a) introducing a methanol feed and process recycle streams to a carbonylation reactor in which methanol and/or a reactive derivative thereof is reacted with carbon monoxide in a liquid reaction composition in said carbonylation reactor to produce acetic acid; the liquid reaction composition comprising a Group VIII metal carbonylation catalyst, methyl iodide co-catalyst, optionally at least one promoter, at least a finite concentration of water, methyl acetate and acetic acid product;

(b) withdrawing liquid reaction composition from said carbonylation reactor and introducing said withdrawn liquid reaction composition into at least one flash separation zone, with or without the addition of heat, to produce a vapour fraction comprising water, acetic acid product, methyl acetate and methyl iodide, and a liquid fraction comprising Group VIII metal carbonylation catalyst and optionally at least one promoter;

(c) recycling said liquid fraction from step (b) to said carbonylation reactor;

(d) introducing said vapour fraction from step (b) into a light ends distillation column;

(e) removing a process stream comprising acetic acid product from said light ends distillation column;

(f) removing a vapour process stream comprising methyl acetate, methyl iodide, water and acetic acid from the head of said light ends distillation column;

(g) condensing said vapour process stream from said head of the light ends distillation column; and (h) recycling at least a portion of said condensed heads vapour process stream from said head of said light ends distillation column as reflux to said light ends distillation column and recycling at least a portion of said condensed vapour process stream to said carbonylation reactor;

in which process the concentration of water in said liquid reaction composition is maintained at a steady-state concentration by at least one process step selected from the group consisting of (i) recovering and disposing of water from at least part of said condensed vapour process stream from said head of said light ends distillation column and recycling the remaining components therefrom to said carbonylation reactor and/or light ends column and (ii) replacing at least a portion of said methanol feed to said carbonylation reactor with a component selected from the group consisting of methyl acetate, dimethyl ether, acetic anhydride and mixtures thereof.

The process of the present invention solves the technical problem defined above by (1) recovering and disposing of water from at least part of the condensed vapour process stream from the head of the light ends distillation column and recycling the remaining components therefrom to the carbonylation reactor and/or light ends column; the criteria necessary for the separation of water from this recycle stream are thus independent of the criteria necessary for the recovery of the acetic acid carbonylation product from the withdrawn liquid reaction composition and/or (2) replacing at least a portion of the methanol feed to the carbonylation reactor with a component selected from the group consisting of methyl acetate, dimethyl ether, acetic anhydride and mixtures thereof; methyl acetate and dimethyl ether are carbonylated to produce acetic acid with net consumption of water from the liquid reaction composition and acetic anhydride removes water from the reaction composition by reaction to produce acetic acid.

In a further embodiment of the present invention, the heads vapour process stream forms two phases when it is condensed; a water-rich phase comprising water with lesser amounts of methyl iodide, acetic acid and methyl acetate and a methyl iodide-rich phase comprising methyl iodide and methyl acetate with lesser amounts of water and acetic acid.

Thus, according to this embodiment of the present invention there is provided a process for the production of acetic acid by the carbonylation of methanol and/or a reactive derivative thereof which process comprises the steps of:

(a') introducing a methanol feed and process recycle streams to a carbonylation reactor in which methanol and/or a reactive derivative thereof is reacted with carbon monoxide in a liquid reaction composition in said carbonylation reactor to produce acetic acid; the liquid reaction composition comprising a Group VIII metal carbonylation catalyst, methyl iodide co-catalyst, optionally at least one promoter, at least a finite concentration of water, methyl acetate and acetic acid product;

(b') withdrawing liquid reaction composition from said carbonylation reactor and introducing said withdrawn liquid reaction composition into at least one flash separation zone, with or without the addition of heat, to produce a vapour fraction comprising water, acetic acid product, methyl acetate and methyl iodide, and a liquid fraction comprising Group VIII metal carbonylation catalyst and optionally at least one promoter;

(c') recycling said liquid fraction from step (b') to said carbonylation reactor;

(d') introducing said vapour fraction from step (b') into a light ends distillation column;

(e') removing a process stream comprising acetic acid product from said light ends distillation column;

(f') removing a vapour process stream comprising methyl acetate, methyl iodide, water and acetic acid from the head of said light ends distillation column;

(g') condensing the vapour process stream from said head of said light ends distillation column to form a water-rich phase comprising water with lesser amounts of methyl iodide, acetic acid and methyl acetate and a methyl iodide-rich phase comprising methyl iodide and methyl acetate with lesser amounts of water and acetic acid; and separating said two phases; and (h') recycling said methyl iodide-rich phase to said carbonylation reactor and returning at least part of said water-rich phase to said light ends distillation column as reflux; in which process the concentration of water in said liquid reaction composition is maintained at a steady-state concentration by at least one process step selected from the group consisting of (i') recovering and disposing of water from at least part of said water-rich phase from said head of said light ends distillation column and recycling the remaining components therefrom to said carbonylation reactor and/or light ends column and (ii') replacing at least a portion of said methanol feed to said carbonylation reactor with a component selected from the group consisting of methyl acetate, dimethyl ether, acetic anhydride and mixtures thereof This embodiment has the advantage that the water concentration in the separated light ends aqueous phase is relatively high, for example in the range 60 to 90% by weight and typically in the range 70 to 85% by weight and also the acetic acid concentration may be relatively low, for example in the range 0 to 10% by weight and typically in the range 1 to 6% by weight, which facilitates recovery of the water therefrom for disposal. The water-rich and methyl iodide-rich phases formed by condensing the vapour process stream from the head of the light ends distillation column may be separated in a decanter.

Suitably, a first portion of the water-rich phase is returned to the light ends distillation column as reflux at a rate of about 0.1 to about 0.7 times the rate of removal of the vapour process stream from the head of the light ends distillation column. Optionally, a portion of the water-rich phase may be returned directly to the carbonylation reactor. The rate at which water is removed from a second portion of the water-rich phase in the water removal column is such as to maintain the concentration of water in the liquid reaction composition in the carbonylation reactor at a steady-state concentration.

In another embodiment of the present invention water may also be recovered and disposed of from a recycle stream comprising water produced further downstream in the purification process, for example during drying of acetic acid product removed from the light ends distillation column. Thus, according to this embodiment of the present invention crude acetic acid product stream removed from the light ends distillation column is introduced into a drying distillation column in which a crude dried acetic acid product stream having a reduced water concentration is separated from a recycle process stream comprising water, at least a part of which is recycled directly or indirectly to the carbonylation reactor and in which the concentration of water in the liquid reaction composition is maintained at a steady-state concentration by the further steps of recovering and disposing of water from at least part of said recycle process stream comprising water removed from the drying distillation column and recycling the remaining components thereof to the carbonylation reactor, the light ends distillation column and/or the drying column. The water-containing process stream may be removed from the head and/or side of the drying column.

Distillation is preferably used for the recovery of water from the process stream from the head of the light ends distillation column and for the optional recovery of water from the recycle process stream from the drying column, but other recovery processes such as semi-permeable membranes and absorption processes may be used. Suitably water is recovered as a base stream in a distillation column and the remaining components as a head stream. The remaining components of the process stream from which the water is recovered may be recycled to the carbonylation reactor and/or one or more of the distillation columns of the process such as the light ends column and/or the drying column. The concentrations of the components in the liquid reaction composition may thereby be maintained at a steady state concentration. Suitably the remaining components recovered from the process stream from the head of the light ends column are recycled to the overheads of the light ends column.

A suitable distillation column for recovery of water from the process stream from the head of the light ends distillation column is a packed stripping column with feed to the head. Suitably, such a stripping column has up to 20 theoretical stages, preferably up to 15 theoretical stages. A tray column might also be used.

A suitable distillation column for the optional recovery of water from the recycle stream from the drying column may have rectification and stripping stages, determined by those skilled in the art to suit the requirements of the process.

Suitably, the distillation column for the recovery of water from the process stream from the head of the light ends distillation column and for the optional recovery of water from the recycle stream from the drying column may be operated at a heads pressure of about 1.2 barg and a base pressure of about 1.3 barg but higher or lower pressures may be used. The operating temperature of the water removal distillation column will depend upon the composition of the feed, heads and base streams and the operating pressure. Typical base temperatures are 120° to 140° C. and typical heads temperatures are 105° to 115° C.

The recovery of water from the process stream from the head of the light ends distillation column may be operated continuously or on a semi-continuous, campaign basis.

In the carbonylation reactor of the present invention, the Group VIII metal carbonylation catalyst is preferably a rhodium or iridium carbonylation catalyst.

When a rhodium carbonylation catalyst is used in the process of the present invention the optional promoter is preferably selected from the group consisting of iodide salts of alkali and alkaline earth metals, quaternary ammonium iodides, and quaternary phosphonium iodides. Suitably the optional promoter may be present up to its limit of solubility.

When an iridium carbonylation catalyst is employed in the process of the present invention the optional promoter is preferably a metal selected from the group consisting of ruthenium, osmium, cadmium, rhenium, zinc, mercury, gallium, indium, tungsten and mixtures thereof. Suitably, the molar ratio of promoter:iridium is [0.5 to 15]:1.

A suitable liquid reaction composition for a rhodium-catalysed carbonylation of methanol comprises 50 to 5000 ppm, preferably 100 to 1500 ppm rhodium; 1 to 30%, preferably 1 to 20%, more preferably 2 to 16% by weight methyl iodide; 0.1 to 15%, preferably 1 to 15%, more preferably less than 14%, yet more preferably less than 11% and still yet more preferably less than 8% by weight water; 0.1 to 70%, preferably 0.5 to 35%, typically up to 5% by weight methyl acetate and balance acetic acid.

A suitable liquid reaction composition for an iridium-catalysed carbonylation of methanol comprises 100 to 6000 ppm iridium, 1 to 20%, preferably 2 to 16% by weight methyl iodide; 1 to 15%, preferably 1 to 10% by weight water; 1 to 70%, preferably 2 to 50% and yet more preferably 3 to 35% by weight methyl acetate and balance acetic acid.

The pressure of the rhodium- and iridium-catalysed carbonylation reactions is suitably in the range 10 to 200 barg, preferably 10 to 100 barg, more preferably 15 to 50 barg. The temperature of the rhodium- and iridium-catalysed carbonylation reactions is suitably in the range 100° to 300° C., preferably in the range 150° to 220° C.

In any of the embodiments of the present invention hereinbefore described, the liquid reaction composition may be withdrawn from the reactor and subjected to one or more pre-flash separation stages with or without the addition of heat to produce one or more pre-flash vapour fractions which are recycled to the carbonylation reactor, before passing remaining composition to a final flash separation zone from which is separated a liquid fraction comprising Group VIII metal carbonylation catalyst and optionally at least one promoter for recycle to the carbonylation reactor and a vapour fraction comprising acetic acid product for purification in the light ends column.

If a single stage flash is used the pressure may be in the range 0 to 3 barg, with a temperature in the range 100° to 150° C. If a two stage flash is used, the pressure in the first flash may be in the range 1 to 10 barg and the pressure of the second flash in the range 0 to 5 barg.

Suitably, the light ends distillation column has up to 40 theoretical stages. The light ends distillation column may be operated at any suitable pressure, for example a heads pressure of about 1.2 barg and a base pressure of about 1.5 barg. The operating temperature of the light ends distillation column will depend upon the composition of the feed, heads and base streams and the operating pressure. Typical base temperatures are in the range 125°–140° C. and typical head temperatures are in the range 105°–115° C.

The process stream comprising acetic acid product may be removed from the light ends distillation column at any suitable point, for example above or below the feed point, or as a liquid or vapour from the base of the light ends distillation column. The process stream comprising acetic acid product removed from the light ends distillation column may be dried, for example, in a drying distillation column, the separated water being either recycled to the carbonylation reactor or removed from the process. The dried acetic acid may then be passed to a heavy ends distillation column in which propionic acid by-product is separated from dry acetic acid.

The proportion of methanol feed replaced by methyl acetate, dimethyl ether and/or acetic anhydride to maintain the concentration of water in the reaction composition at a steady-state concentration may be up to about 5% molar, for example about 1 mol %.

The water recovered from the process stream from the head of the light ends distillation column and optionally recovered from the drying column is disposed of from the process. However, this water may contain acetic acid which may require removal before disposal of the water. The carboxylic acid-contaminated aqueous effluent may be purified prior to disposal by removal of carboxylic acid, for example by distillation, for use in the process or elsewhere. Alternatively, the acetic acid may be neutralised or otherwise removed by reaction before disposal of the water.

In a preferred embodiment of the present invention, acetic acid-contaminated aqueous effluent from the light ends column heads process stream and optionally from the drying column may be purified of acetic acid by reactive distillation in which the acetic acid is reacted with at least one $C_1$ to $C_3$ alcohol.

Thus, according to another aspect of the present invention there is provided a process for the purification of a carboxylic acid-contaminated aqueous effluent stream which process comprises feeding the effluent stream to a reactive distillation column having in an intermediate zone thereof, a fixed bed esterification catalyst and being provided with (i) at a position above the top of the catalyst zone an aqueous effluent stream feed point, (ii) below the bottom of the catalyst zone an alcohol feed point, (iii) an overhead vapour take-off point, and (iv) a base liquid take-off point, the effluent stream being fed to the reactive distillation column at the effluent stream feed point, at least one $C_1$ to $C_3$ alcohol being fed to the reactive distillation column at the alcohol feed point, the carboxylic acid and alcohol being conjoined in the catalyst zone to react to form carboxylate ester of the alcohol, there being removed from the overhead take-off point a vapour fraction comprising carboxylate ester of the alcohol, and there being removed from the base liquid take-off point a liquid stream for disposal comprising water containing significantly less carboxylic acid than in the carboxylic acid-contaminated aqueous effluent.

According to this aspect of the present invention the carboxylic acid-contaminated aqueous effluent stream may be discharged from any process for the production of carboxylic acid such as hydrocarbon oxidation and carbonylation reactions. Suitable sources of carboxylic acid-contaminated aqueous effluent stream are processes for the production of acetic acid by butane oxidation, naphtha oxidation and carbonylation of methanol, methyl acetate, dimethyl ether and/or reactive derivatives thereof The carboxylic-acid contaminated aqueous effluent stream may also be discharged from processes in which the carboxylic acid is a reactant or solvent for example, from a process for the production of vinyl acetate from acetic acid. In a preferred embodiment the aqueous effluent stream is derived from the condensed vapour process stream from the head of the light ends column, particularly a separated aqueous phase, of a carbonylation process for the production of acetic acid by carbonylation of methanol and/or a reactive derivative thereof.

The carboxylic acid-contaminated aqueous effluent stream may comprise one or more carboxylic acids, suitably having 1 to 10 carbon atoms, preferably 1 to 6 carbon atoms and is most preferably formic, acetic and/or propionic acid. The carboxylic acid-contaminated aqueous effluent stream may comprise up to 50% by weight carboxylic acid, preferably up to 10% by weight carboxylic acid. The carboxylic acid-contaminated aqueous effluent stream may additionally comprise (i) esters of the carboxylic acid for example methyl acetate, at a concentration for example, of up to 20% by weight; (ii) alcohols, for example methanol, at a concentration for example, of up to 10% by weight; and (iii) alkyl halides, for example methyl iodide, at a concentration for example, of up to 5% by weight.

According to this aspect of the present invention, purification of the carboxylic acid-contaminated aqueous effluent is effected in a reactive distillation column. Such a column may be briefly described as one in which concurrent formation and distillation of the product occurs. Reactive distillation columns are not new. Thus, the production of methyl acetate by reaction of glacial acetic acid with methanol in a reactive distillation column is described, for example, in EP-0473688-B1 and EP-0105885-B1.

In the process of the present invention there is used a reactive distillation column having an intermediate zone thereof, a fixed bed esterification catalyst, the column being provided with (i) at a position above the top of the catalyst zone an aqueous effluent stream feed point, (ii) below the bottom of the catalyst zone an alcohol feed point, (iii) an overhead vapour take-off point, and (iv) a base liquid take-off point. The fixed bed esterification catalyst is preferably an acid catalyst which may take the form of a mineral acid, for example sulphuric acid or phosphoric acid, supported on a suitable support. Alternatively the catalyst may be the acid form of a clay, a crystalline alumninosilicate, for example ZSM-5, or an ion-exchange resin, for example Amberlyst 15. Suitable catalysts or catalyst supports are those marketed by Sulzer Chemtech under the trade mark KATAPAK which have an ion exchange resin catalyst within an open crossflow structure. The fixed bed esterification catalyst may be mounted in column sections for ease of removal from the distillation column. Preferably, the reactive distillation zone has upper and lower fractuation zones above and below the fixed bed esterification catalyst.

At least one $C_1$ to $C_3$ alcohol is used, preferably methanol, ethanol and/or isopropanol more prefereably methanol. Commercially available methanol may suitably be employed. The $C_1$ to $C_3$ alcohol is suitably fed in an amount sufficient to react completely with the carboxylic acid in the effluent stream. Preferably, an excess of alcohol over stoichiometric is fed.

Carboxylic acid-contaminated aqueous effluent is fed to the reactive distillation column at the effluent stream feed point. Concurrently, at least one $C_1$ to $C_3$ alcohol is fed at the alcohol feed point. The carboxylic acid and alcohol are conjoined in the catalyst zone to react to form carboxylate ester of the alcohol. The reactive distillation column is maintained under conditions of temperature and pressure such that there is removed from the overhead take-off point a vapour fraction comprising carboxylate ester of the alcohol and from the base liquid take-off point a liquid stream comprising water containing significantly less carboxylic acid than in the aqueous effluent feed. The vapour fraction may comprise in addition to carboxylate ester of the alcohol, one or more of water, unconsumed alcohol, carboxylic acid and other contaminants such as alkyl halide. The vapour fraction may be condensed and all or a part thereof recycled to the process from which the aqueous effluent stream is removed. Part of the condensed vapour from the overhead take-off point may be returned, if desired, to the reactive distillation column as reflux. The liquid stream removed from the base liquid take-off point comprises water suitably containing less than 5%, typically less than 1%, preferably less than 0.5%, more preferably less than 0.1% weight carboxylic acid. Desirably, the liquid stream will contain substantially no alcohol and carboxylate ester of the alcohol. The liquid stream may be discharged to waste with less risk of environmental pollution than hitherto. Advantageously, also the carboxylic acid recovered therefrom in the form of carboxylate ester may be recycled as feedstock to a compatable process, for example to a carboxylic acid production process from which the aqueous effluent stream is removed, rather than being wasted. Thus, methyl acetate may be recycled to a carbonylation process for the production of acetic acid.

The reactive distillation column is suitably operated without reflux, at pressures up to 1.5 barg and a temperature range in the column up to about 140° C. at the base and up to about 100° C. at the head of the column. Higher pressures may be used with advantage.

Figure 1:
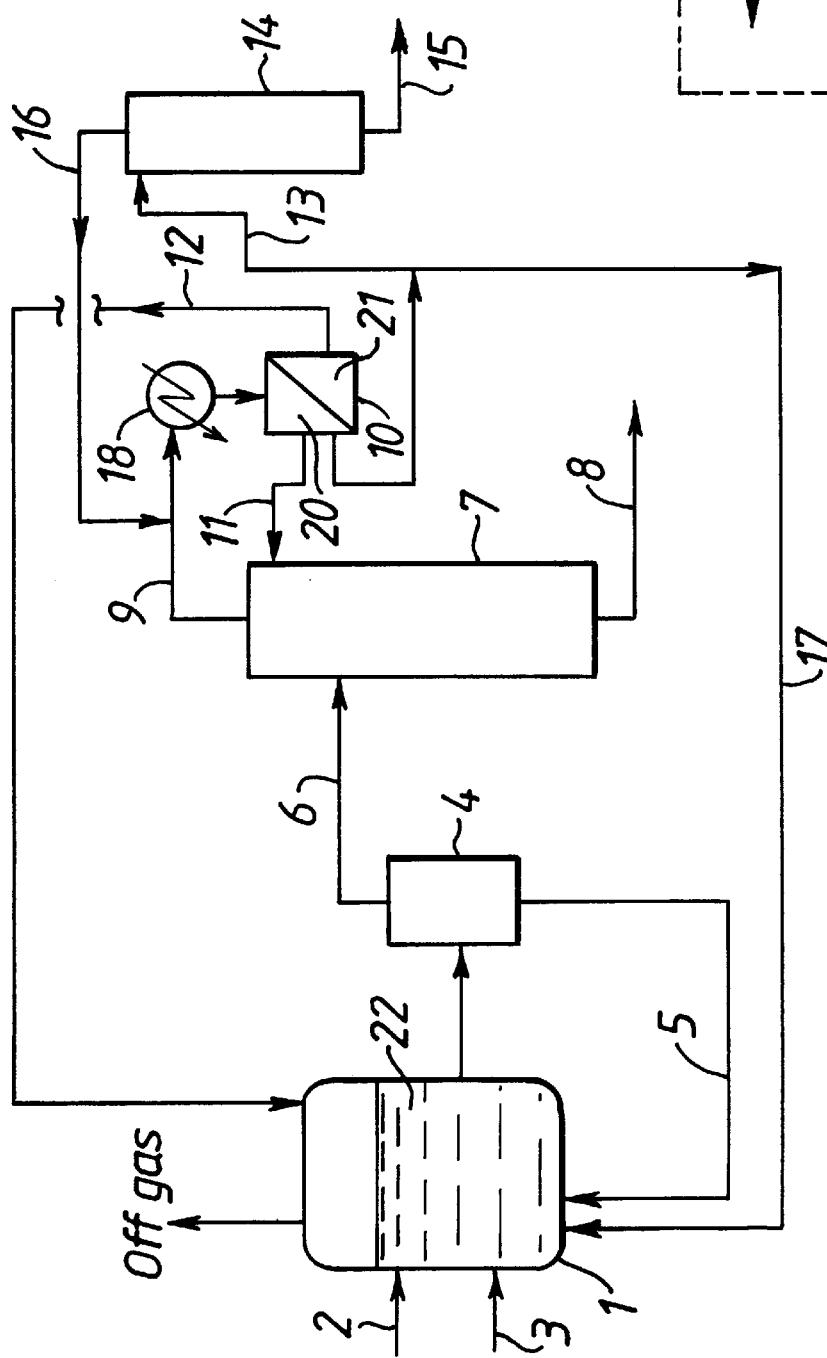

The invention will now be illustrated by way of example only by reference to FIGS. 1 and 2. FIG. 1 represents in schematic form a flow diagram of an iridium-catalysed carbonylation process according to the present invention. FIG. 2 represents a reactive distillation column for recovery of water from the light ends overhead water-rich phase.

In FIG. 1 a carbonylation reactor (1) is provided with means (2) for introducing carbon monoxide to the reactor and means (3) for introducing methanol feed to the reactor. In use, the carbonylation reactor (1) contains a liquid reaction composition (22) comprising iridium carbonylation catalyst, methyl iodide co-catalyst, optionally at least one promoter selected from the group consisting of ruthenium, osmium, cadmium, rhenium, zinc, mercury, gallium, indium and tungsten, a finite concentration of water of at least 0.1% by weight, methyl acetate and acetic acid. In use, the reactor is maintained at a pressure of 10 to 100 barg and at a temperature of 100° to 300° C. In use, the methanol is present in the liquid reaction composition predominantly as methyl acetate and reacts with the carbon monoxide to produce acetic acid. In use, liquid carbonylation reaction composition is withdrawn from the carbonylation reactor (1) and is introduced to flash separation zone (4) operated at a pressure below that of the carbonylation reactor (1) (for example 0 to 20 barg) to produce a vapour fraction comprising water, acetic acid and the majority of the methyl acetate and methyl iodide and a liquid fraction comprising iridium carbonylation catalyst and optionally at least one promoter. The liquid fraction is recycled to the carbonylation reactor (1) via line (5) while the vapour fraction is passed from flash zone (4) to the light ends distillation column (7) along line (6). A vapour process stream comprising methyl acetate, methyl iodide, water and acetic acid is taken from the head of the light ends distillation column (7). The vapour process stream is passed along line (9) to a condenser (18) where the vapour process stream is condensed before being passed to decanter (10) wherein is formed a water-rich phase (20) comprising water with lesser amounts of methyl iodide and methyl acetate and a methyl iodide-rich phase (21) comprising methyl iodide and methyl acetate with a lesser amount of water. The methyl iodide-rich phase is recycled to the carbonylation reactor (1) along line (12). A first portion of the water-rich phase is returned to the light ends distillation column (7) as reflux along line (11) while a second portion of the water-rich phase is recycled to the carbonylation reactor (1) along line (17). A third portion of the water-rich phase is introduced to a water removal distillation column (14) along line (13). A stream comprising water with small amounts of acetic acid is removed from the base of the water removal distillation column via line (15) and is disposed of from the process. A stream comprising the remainder of the water-rich phase is removed from the head of the water removal distillation column (14) and is recycled to the light ends distillation column overheads along line (16) and conjoined with the light ends vapour process stream.

Alternatively as shown in FIG. 2, the water removal column (14) may be a reactive distillation column additionally having upper (32) and lower (33) fractionation zones and, in an intermediate zone thereof, a fixed bed esterification catalyst (30) and at a position intermediate the bottom of the column and the bottom of the catalyst zone a methanol feed point (31) as well as the water-rich phase feed line (13). The acetic acid in the water rich phase introduced to the column (14) and the methanol introduced through methanol feed point (31) are conjoined in the catalyst zone (30) to react to form methyl acetate. The column (14) is maintained under conditions of temperature and pressure such that there is removed from the overhead take-off point a vapour fraction comprising methyl acetate and from the base liquid take-off point a liquid stream comprising water containing less than 1% weight acetic acid.

A crude acetic acid product stream is taken from the base of light ends distillation column along line (8) and may be further purified by conventional means (not shown) to remove, for example, water, iodide, oxidisable impurities and propionic acid. Such purification may include the use of a drying column from which is recovered a recycle process stream comprising water, at least a part of which is recycled directly or indirectly to the carbonylation reactor. Water may be recovered and disposed of from at least part of the recycle process stream comprising water from the drying distillation column and the remaining components thereof may be recycled to the carbonylation reactor, the light ends distillation column and/or the drying column. The water recovered for the drying column may also be purified by reactive distillation according to the process of the present invention.

It is envisaged that off-specification acetic acid containing water may be introduced to the process, for example, to the drying column. Also, there may be direct and/or indirect ingress of water into the reactor through leaks such as from pump seals and/or condensers or coolers which use water as coolant.

The concentration of water in the liquid reaction composition is maintained at a steady-state concentration by recovering and disposing of water from the water-rich phase condensed from the vapour process stream from the head of the light ends distillation column and recycling the remaining components therefrom to the light ends distillation column and reactor and/or by replacing at least a portion of the methanol feed to the carbonylation reactor with a component selected from the group consisting of methyl acetate, dimethyl ether, acetic anhydride and mixtures thereof.

To illustrate the reactive distillation embodiment of the present invention, the following experiments were performed.

In the Examples there was used a synthetic aqueous effluent mixture designed to mimic the aqueous effluent (apart from the absence of methyl iodide) from a process for the production of acetic acid by carbonylation of methanol in the presence of an iridium carbonation catalyst. The composition of the synthetic aqueous effluent was:

| | |
|---|---|
| water ($H_2O$) | 81% weight |
| methanol (MeOH) | 1% weight |
| methyl acetate (MeOAc) | 13% weight |
| acetic acid (AcOH) | 5% weight |

This was fed in to the top of a reactive distillation column, to which methanol was also fed below the catalyst zone. The column was operated at atmospheric pressure and without reflux. The reaction zone of the column consisted of Sulzer packing incorporating about 245 g Amberlyst A15, the bed volume being about 1.17 liters. The reactive distillation column comprised three sections, an upper fractionation zone of 1 inch diameter containing 5 glass Oldershaw trays; a middle reaction zone of 2 inch diameter and a lower distillation zone of 2 inch diameter containing 8 PTFE trays.

EXAMPLE 1

The aqueous effluent was fed at a rate of approx. 1.5 l/h, the MeOH:AcOH molar ratio was approximately 8:1 and the temperature in the catalyst zone was 81° C. The compositions of the heads take-off (HTO) and bottoms take-off (BTO) were as follows:

| Fraction | $H_2O$ (wt %) | MeOH (wt %) | MeOAc (wt %) | AcOH (wt %) | Flow Rate (g/h) |
|---|---|---|---|---|---|
| HTO | 25 | 18 | 57 | <0.1 | 450 |
| BTO | 85 | 15 | 0 | <0.1 | 1180 |

It is apparent that essentially all of the acetic acid had been removed from the effluent stream. The temperature in the base however was 88° C. due to the methanol present. Not enough boil up was achieved in the column but this was at the reboiler limit. Accordingly, the Example was repeated (Example 2) at half the feed rate.

EXAMPLE 2

The aqueous effluent was fed at a rate of approx. 700 ml/h, the MeOH:AcOH molar ratio was approximately 11:1 and the temperature in the catalyst zone was 81° C. The compositions of the take-off streams were as follow:

| Fraction | $H_2O$ (wt %) | MeOH (wt %) | MeOAc (wt %) | AcOH (wt %) | Flow Rate (g/h) |
|---|---|---|---|---|---|
| HTO | 31 | 31 | 38 | <0.1 | 350 |
| BTO | 99.98 | 0 | 0 | <0.1 | 450 |

It is apparent that essentially all the acetic acid had been removed from the effluent stream. The base temperature was 98.7° C., and the base stream was essentially water. However, this was achieved at the expense of a large excess of methanol and also a significant amount of water in the HTO. A further example (Example 3) was carried out to examine the effect of reducing the methanol feed at this aqueous feed rate.

EXAMPLE 3

The aqueous effluent was fed at a rate of approx. 780 ml/h, the MeOH:AcOH molar ratio was approximately 3:1 and the temperature in the catalyst zone was 82.5° C. The compositions of the take-off streams were as follows:

| Fraction | $H_2O$ (wt %) | MeOH (wt %) | MeOAc (wt %) | AcOH (wt %) | Flow Rate (g/h) |
|---|---|---|---|---|---|
| HTO | 25 | 22 | 52 | <0.1 | 270 |
| BTO | 99.9 | 0 | 0 | <0.1 | 550 |

It is apparent that essentially all the acetic acid had been removed from the effluent stream. The base temperature was 98° C., and the base stream was essentially water.

We claim:

1. A process for the production of acetic acid by the carbonylation of methanol and/or a reactive derivative thereof which process comprises the steps of:

(a) introducing a methanol feed and process recycle streams to a carbonylation reactor in which methanol and/or a reactive derivative thereof is reacted with carbon monoxide in a liquid reaction composition in said carbonylation reactor to produce acetic acid; the liquid reaction composition comprising an iridium carbonylation catalyst, methyl iodide co-catalyst, at least one promoter selected from ruthenium, osmium, cadmium, rhenium, zinc, mercury, gallium, indium, and tungsten, from 0.1 to 10% by weight water, methyl acetate and acetic acid product;

(b) withdrawing liquid reaction composition from said carbonylation reactor and introducing said withdrawn liquid reaction composition into at least one flash separation zone, with or without the addition of heat, to produce a vapour fraction comprising water, acetic acid product, methyl acetate and methyl iodide, and a liquid fraction comprising iridium carbonylation catalyst and at least one promoter;

(c) recycling said liquid fraction from step (b) to said carbonylation reactor;

(d) introducing said vapour fraction from step (b) into a light ends distillation column;

(e) removing a process stream comprising acetic acid product from said light ends distillation column;

(f) removing a vapour process stream comprising methyl acetate, methyl iodide, water and acetic acid from the head of said light ends distillation column;

(g) condensing said vapour process stream from said head of the light ends distillation column; and (h) recycling at least a portion of said condensed heads vapour process stream from said head of said light ends distillation column as reflux to said light ends distillation column and recycling at least a portion of said condensed vapour process stream to said carbonylation reactor;

in which process the concentration of water in said liquid reaction composition is maintained at a steady-state concentration by at least one process step selected from the group consisting of (i) recovering and disposing of water from at least part of said condensed vapour process stream from said head of said light ends distillation column and recycling the remaining components therefrom to said carbonylation reactor and/or light ends column and (ii) replacing at least a portion of said methanol feed to said carbonylation reactor with a component selected form the group consisting of methyl acetate, dimethyl ether, acetic anhydride and mixtures thereof.

2. A process as claimed in claim 1 which comprises the steps of:

(a') introducing a methanol feed and process recycle streams to a carbonylation reactor in which methanol and/or a reactive derivative thereof is reacted with carbon monoxide in a liquid reaction composition in said carbonylation reactor to produce acetic acid; the liquid reaction composition comprising an iridium carbonylation catalyst, methyl iodide co-catalyst, at least one promoter selected from ruthenium, osmium, cadmium, rhenium, zinc, mercury, gallium, indium, and tungsten, from 0.1 to 10% by weight water, methyl acetate and acetic acid product;

(b') withdrawing liquid reaction composition from said carbonylation reactor and introducing said withdrawn liquid reaction composition into at least one flash separation zone, with or without the addition of heat, to produce a vapour fraction comprising water, acetic acid product, methyl acetate and methyl iodide, and a liquid fraction comprising iridium carbonylation catalyst and at least one promoter;

(c') recycling said liquid fraction from step (b') to said carbonylation reactor;

(d') introducing said vapour fraction from step (b') into a light ends distillation column;

(e') removing a process stream comprising acetic acid product from said light ends distillation column;

(f') removing a vapour process stream comprising methyl acetate, methyl iodide, water and acetic acid from the head of said light ends distillation column;

(g') condensing the vapour process stream from said head of said light ends distillation column to form a water-rich phase comprising water with lesser amounts of methyl iodide, acetic acid and methyl acetate and a methyl iodide-rich phase comprising methyl iodide and methyl acetate with lesser amounts of water and acetic acid; and separating said two phases; and (h') recycling said methyl iodide-rich phase to said carbonylation reactor and returning at least part of said water-rich phase to said light ends distillation column as reflux;

in which process the concentration of water in said liquid reaction composition is maintained at a steady-state concentration by at least one process step selected from the group consisting of (i') recovering and disposing of water from at least part of said water-rich phase from said head of said light ends distillation column and recycling the remaining components therefrom to said carbonylation reactor and/or light ends column and (ii') replacing at least a portion of said methanol feed to said carbonylation reactor with a component selected from the group consisting of methyl acetate, dimethyl ether, acetic anhydride and mixtures thereof.

3. A process as claimed in claim 2 in which water is recovered from the process stream from the head of the light ends distillation column by distillation.

4. A process as claimed in claim 3 in which the water is removed in a distillation column operated with a base temperature in the range 120° to 140° C. and a heads temperature in the range 105° to 115° C.

5. A process as claimed in claim 3 in which the water is removed in a distillation column operated at a heads pressure of about 1.2 barg and a base pressure of about 1.3 barg.

6. A process as claimed in claim 3 in which water is recovered as a base stream and the remaining components as a heads stream which is recycled to the overheads of the light ends distillation column.

7. A process as claimed in claim 6 in which water is recovered from the process stream from the head of the light ends distillation column in a packed stripping column with feed to the head.

8. A process as claimed in claim 2 in which said water-rich phase comprises acetic acid and in which water from at least part of said water-rich phase from said head of said light ends distillation column is recovered and purified prior to disposal by feeding at least part of said water-rich phase from said head of said light ends distillation column to a reactive distillation column having in an intermediate zone thereof, a fixed bed esterification catalyst and being provided with (i) at a position above the top of the catalyst zone an aqueous effluent stream feed point, (ii) below the bottom of the catalyst zone an alcohol feed point, (iii) an overhead vapour take-off point, and (iv) a base liquid take-off point; at least part of said water-rich phase being fed to the reactive distillation column at the effluent stream feed point, at least one $C_1$ to $C_3$ alcohol being fed to the reactive distillation column at the alcohol feed point, the acetic acid and alcohol being conjoined in the catalyst zone to react to form acetate ester of the alcohol, there being removed from the overhead take-off point a vapour fraction comprising acetate ester, and there being removed from the base liquid take-off point a liquid stream for disposal comprising water containing significantly less than acetic acid than in said water-rich phase.

9. A process as claimed in claim 8 in which said base liquid take-off stream comprises less than 1% weight acetic acid.

10. A process as claimed in claim 8 in which said at least one $C_1$ to $C_3$ alcohol is methanol.

11. A process as claimed in claim 1 in which water is recovered and disposed of from the process stream comprising acetic acid product removed from the light ends distillation column.

12. A process as claimed in claim 11 in which the process stream comprising acetic acid product removed from the light ends distillation column is introduced into a drying distillation column in which a crude dried acetic acid product stream having a reduced water concentration is separated from a recycle process stream comprising water, at least a part of which is recycled directly or indirectly to the carbonylation reactor and in which the concentration of water in the liquid reaction composition is maintained at a steady-state concentration by the farther steps of recovering and disposing of water from at least part of said recycle process stream comprising water removed from the drying distillation column and recycling the remaining components thereof to the carbonylation reactor, the light ends distillation column and/or the drying column.

13. A process as claimed in claim 12 in which the water from said at least part of said recycle process stream comprising water removed from the drying distillation column comprises acetic acid and is purified by feeding at least part of said recycle process stream to a reactive distillation column having in an intermediate zone thereof, a fixed bed esterification catalyst and being provided with (i) at a position above the top of the catalyst zone an aqueous effluent stream feed point, (ii) below the bottom of the catalyst zone an alcohol feed point, (iii) an overhead vapour take-off point, and (iv) a base liquid take-off point, said process stream comprising water removed from the drying distillation column being fed to the reactive distillation column at the effluent stream feed point, at least one $C_1$ to $C_3$ alcohol being fed to the reactive distillation column at the alcohol feed point, the acetic acid and alcohol being conjoined in the catalyst zone to react to form acetate ester of the alcohol, there being removed from the overhead take-off point a vapour fraction comprising acetate ester, and there being removed from the base liquid take-off point a liquid stream for disposal comprising water containing significantly less acetic acid than in the recycle process stream feed.

14. A process as claimed in claim 13 in which said base liquid take-off stream comprises less than 1% weight acetic acid.

15. A process as claimed in claim 13 in which said at least one $C_1$ to $C_3$ alcohol is methanol.

16. A process as claimed in claim 1 in which up to about 5% molar of said methanol feed to said carbonylation reactor is replaced with a component selected from the group consisting of methyl acetate, dimethyl ether, acetic anhydride and mixtures thereof to maintain the concentration of water in the reaction composition at a steady-state concentration.

17. A process for the purification of a carboxylic acid-contaminated aqueous effluent stream which process comprises feeding the effluent stream to a reactive distillation column having in an intermediate zone thereof, a fixed bed esterification catalyst and being provided with (i) at a position above the top of the catalyst zone an aqueous effluent stream feed point, (ii) below the bottom of the catalyst zone an alcohol feed point, (iii) an overhead vapour take-off point, and (iv) a base liquid take-off point, the effluent stream being fed to the reactive distillation column at the effluent stream feed point, at least one $C_1$ to $C_3$ alcohol being fed to the reactive distillation column at the alcohol feed point, the carboxylic acid and alcohol being conjoined in the catalyst zone to react to form carboxylate ester of the alcohol, there being removed from the overhead take-off point a vapour fraction comprising carboxylate ester, and there being removed from the base liquid take-off point a liquid stream for disposal comprising water containing significantly less carboxylic acid than in the aqueous effluent stream.

18. A process as claimed in claim 17 in which said base liquid take-off stream comprises less than 1% weight carboxylic acid.

19. A process as claimed in claim 17 in which said carboxylic acid contaminant is at least one carboxylic acid having 1 to 10 carbon atoms.

20. A process as claimed in claim 19 in which said carboxylic acid is at least one of formic acid, acetic acid and propionic acid.

21. A process as claimed in claim 20 in which said at least one $C_1$ to $C_3$ alcohol is methanol.

22. A process as claimed in claim 9 in which there is removed from the base liquid take-off point a liquid stream for disposal comprising water containing less than 0.5% weight carboxylic acid, preferably less than 0.1% weight carboxylic acid.

23. A process as claimed in claim 14 in which there is removed from the base liquid take-off point a liquid stream for disposal comprising water containing less than 0.5% weight carboxylic acid, preferably less than 0.1% weight carboxylic acid.

24. A process as claimed in claim 18 in which there is removed from the base liquid take-off point a liquid stream for disposal comprising water containing less than 0.5% weight carboxylic acid, preferably less than 0.1% weight carboxylic acid.

25. A process as claimed in any one of claims 2 to 16 in which said Group VIII metal is iridium.

26. A process according to claim 1 wherein the promoter is selected from ruthenium and osmium.

27. A process according to claim 1 wherein the molar ratio of promoter to iridium is (0.5 to 15):1.

* * * * *